United States Patent [19]

Langvad, deceased

[11] Plant 4,165

[45] Dec. 13, 1977

[54] BLUEGRASS PLANT

[75] Inventor: Bjarne Johan Langvad, deceased, late of Landskrona, Sweden, by Brita Langvad, administratrix

[73] Assignee: W. Weibull AB, Landskrona, Sweden

[21] Appl. No.: 736,884

[22] Filed: Oct. 29, 1976

[51] Int. Cl.[2] ..... A01H 5/12

[52] U.S. Cl. ..... Plt./88

[58] Field of Search ..... Plt./88

*Primary Examiner*—Robert E. Bagwill

[57] ABSTRACT

A Kentucky bluegrass plant which exhibits an attractive dark green color, rather narrow leaves and low rhizomatous growth habit and high density of shoots. It has a very large seed size and shows good resistance to Helminthosporium leaf spot, Mildew and Stripe smut diseases.

3 Drawing Figures

BACKGROUND OF THE INVENTION

This invention relates to a new and distinct variety of bluegrass plant, the novel characteristics of which reside particularly in its very attractive dark green color, which is maintained well throughout the growing season, a rather narrow leaf blade, large seed size and good resistance to common turf diseases, particularly leaf spot, stripe smut and mildew.

This new variety was discovered in plant material collected at the Lidingo Golf Course, Sweden. Selections within the plant material have been made towards a plant with dark green color, rather narrow leaves and good resistance to Helminthosporium. This plant was reproduced asexually by vegetative reproduction. After growth in a greenhouse, the vegetatively reproduced plants were transferred to field nurseries for increase and subsequent turf evaluation. Progeny tests were conducted and showed that the plant could be reproduced asexually by means of disseminules. The plant was thereafter identified as WK 411 bluegrass.

WK 411 exhibits a unique combination of characteristics which distinguishes it from all other varieties of which applicant is aware. Of special moment is its attractive dark green color in combination with narrow leaves and excellent resistance to stripe smut disease caused by the fungus *Ustilago striiformis.* The new variety exhibits good to excellent resistance to powdery mildew disease caused by the fungus *Erysiphe graminis* and to leaf spot caused by the fungus *Helminthosporium vagans.* WK 411 Kentucky bluegrass greens up early in the spring and maintains an attractive dark green color throughout the growing season. The variety is highly apomictic and has a turf-type growth habit tolerant to moderately close mowing.

A primary object of the invention is to provide a new and distinct bluegrass plant having the desirable characteristics referred to above and to be described in detail below.

Other objects and advantages of the invention will become more fully apparent from the following detailed description when taken in conjunction with the accompanying illustrations in which.

PLANT DESCRIPTION

Figure 1:
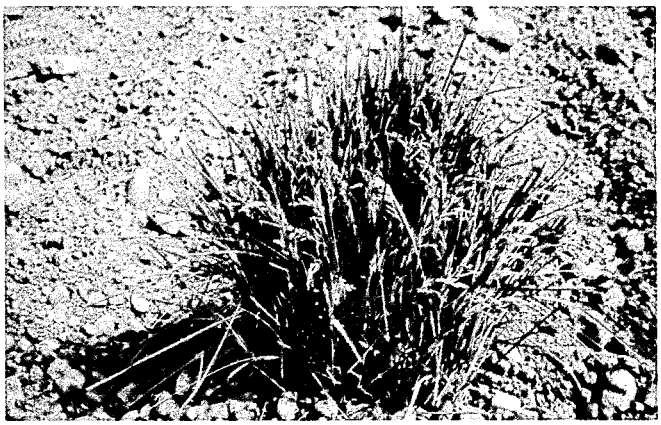
FIG. 1 shows a plant of the new variety approximately 4 weeks before the flowering stage.
Figure 2:
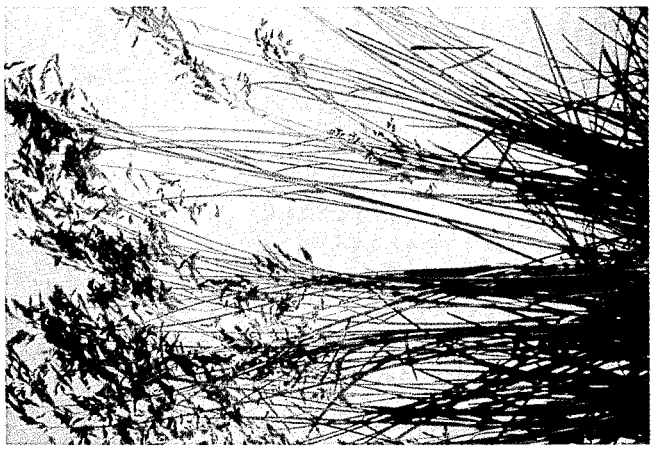
FIG. 2 shows a plant of the new variety about 2 weeks after the completion of the flowering stage.
Figure 3:
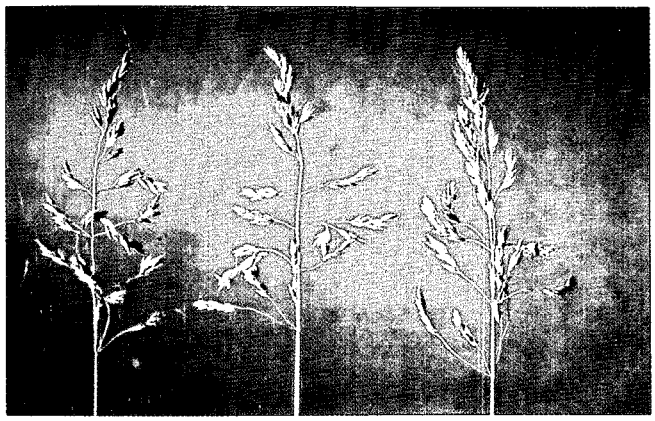
FIG. 3 shows a panicle of the new variety about 2 weeks after completion of the flowering stage.

WK 411 bluegrass (*Poa pratensis*) is a perennial with creeping rhizomes, forming a dense, moderately low-growing compact turf. The variety possesses the following unique combination of characteristics:

1. Very good resistance to the stripe smut disease caused by the fungus *Ustilago striiformis.*
2. Good resistance to the leaf spot disease caused by the fungus *Helminthosporium vagans.*
3. Good resistance to powdery mildew caused by the fungus *Erysiphe graminis.*
4. Very good cold tolerance and winter survival.
5. An attractive dark green color during the entire growing season from early spring to late fall.
6. A narrow leaf blade, which makes WK 411 compatible with fine-leaved grasses, e.g., red fescue in mixtures.
7. Good rhizome and tiller development, forming a turf of superior density and good spreading ability.
8. Prostrate growth habit allowing close mowing.
9. Very good turf performance.
10. Very large seed, thousand kernel weight 0.45 g.

Morphological Description

The plants of the new variety described below were grown in South Sweden, lat. 56° N.

Roots: Rhizomes of medium length, average 52 mm., see Table 1, below:

Table 1

Rhizome Development in 3-month Old Kentucky Bluegrass Plants (South Sweden)

| Variety | No. of rhizomes Average per plant | Total length in mm. of rhizomes Average per plant | Length in average per rhizome, mm. |
|---|---|---|---|
| Merion | 2.4 | 79 | 33 |
| WK 411 | 2.9 | 151 | 52 |
| Sydsport | 2.7 | 168 | 62 |

Leaves: Flag leaf is relatively short, dark green with blades 4–5 mm. wide and 47–67 mm. long. WK 411 has weak anthocyanin coloring of the leaf sheath in the young stage. Leaf sheath base is keeled, glabrous and glaucous. The ligule is of medium size, slightly pointed and is hairy.

Straw: Of medium length, plant height 65–70 cm.

Panicle: Pyramidal with main axis erect and top slightly drooping. Side axis at the bottom are horizontal. Panicle length 120–130 mm. Panicle slightly anthocyan colored. Lemmas are glabrous with indistinct intermediate nerves and scant basal webbing. The keel and lateral nerves are slightly pubescent. For further floret characteristics, see Table 2, below:

Table 2

Floret Characteristics of WK 411 Bluegrass (Oregon Grown)

| | Character | Description |
|---|---|---|
| 1. | Intermediate nerves on lemma | Indistinct |
| 2. | Lemma color | Light straw color to uniform brown, lighter seeds often with dark spot near base. |
| 3. | Lemma margins and apex | Apex semi-flared from sharp keel-tapered to medium point in side view. Wide hyaline margins especially in basal florets. Margins tend to enclose palea in middle and terminal florets. |
| 4. | Lemma texture | Finely granular |
| 5. | In lateral plane - floret shape plus thickness or plumpness | Lemma evenly arched. Mass of seed greatest about middle. |
| 6. | Palea | Finely granular, coarse teeth extending to near apex. |
| 7. | Length | 2.4 to 3.5 mm. (average 2.9 mm.). |
| 8. | Width | 0.6 to 0.8 mm. (average 0.7 mm.). |

Seed: Very large seeded, average length 3.0 mm. and width 0.7 mm., see Table 3, below. WK 411 contains about 1,008,000 seeds per pound (0.450 grams per 1000 seeds) compared with Merion bluegrass, which is said to contain 2,100,000 seeds per pound.

Table 3

Seed Measurements South Sweden 1971–73

| Variety | Seed Length, mm. | Seed Width, mm. |
|---|---|---|
| WK 411 | 3.03 | 0.72 |
| Fylking | 2.80 | 0.73 |
| Merion | 2.31 | 0.74 |
| Windsor | 2.20 | 0.59 |
| Nugget | 3.33 | 0.77 |

For morphological comparisons see Table 4, below:

Table 4.

| Planted 1971 | Plant height, mm | Flag leaf length, mm | Flag leaf width, mm | Panicle length, mm |
|---|---|---|---|---|
| Variety | 12 . 6 . 73 | 4 . 6. 73 | 4 . 6 . 73 | 12 . 6 . 73 |
| WK 411 | 695 | 66.5 | 5.2 | 130.7 |
| Baron | 619 | 36.5 | 5.0 | 82.8 |
| Fylking | 720 | 65.8 | 4.8 | 123.9 |
| Newport | 868 | 80.3 | 4.7 | 129.7 |
| Nugget | 500 | 49.5 | 4.7 | 71.8 |
| Merion | 828 | 87.8 | 5.5 | 120.3 |
| Primo | 841 | 55.8 | 4.6 | 119.9 |

| Planted 1973 | Ear emergence | | Flowering | | Plant height, mm | | Flag leaf length, mm | Panicle length, mm |
|---|---|---|---|---|---|---|---|---|
| Variety | 1974 | 1975 | 1974 | 1975 | 1–7–74 | 3–7–75 | 27–5–75 | 3–7–75 |
| WK411 | 15.5 | 23.5 | 4.6 | 10.6 | 654 | 714 | 47.1 | 131.6 |
| Belturf | 15.5 | 20.5 | 8.6 | 13.6 | 688 | 770 | 59.8 | 118.8 |
| Adelphi | 13.5 | 20.5 | 5.6 | 13.6 | 548 | 833 | 41.4 | 114.5 |

Turf Performance

Turf performance and spring color ratings for WK 411 and other Kentucky bluegrasses for the years 1969–1973 at New Brunswick, New Jersey, are presented in Table 5, below:

Table 5.

| Variety | Turf Quality Ratings 9 = Best 1969 | 1970 | 1971 | 1972 | 1973 | Spring Color 9 = Best April 10, 1972 |
|---|---|---|---|---|---|---|
| Majestic | 7.9 | 7.9 | 6.8 | 6.5 | 6.8 | 8.0 |
| WK-411 | 6.8 | 6.8 | 6.3 | 6.1 | 6.6 | 5.7 |
| Fylking | 7.3 | 7.2 | 6.7 | 6.9 | 6.5 | 5.0 |
| Belturf | 6.8 | 7.1 | 6.3 | 5.3 | 6.3 | 5.0 |
| Pennstar | 7.2 | 7.0 | 6.5 | 6.8 | 6.2 | 5.0 |
| Nugget | 8.1 | 6.9 | 6.5 | 4.9 | 5.2 | 1.0 |
| Windsor | 4.5 | 4.5 | 4.7 | 4.2 | 4.8 | 4.7 |
| Merion | 6.6 | 6.9 | 4.7 | 3.2 | 3.34 | 3.3 |
| Primo | 5.6 | 4.3 | 3.8 | 2.9 | 2.9 | 2.7 |
| Park | 4.7 | 3.9 | 3.6 | 2.9 | 2.3 | 5.3 |
| Delta | 2.9 | 2.5 | 2.5 | 2.1 | 1.7 | 4.0 |
| S. Dak. Cert. | 3.4 | 2.7 | 2.4 | 1.9 | 1.6 | 3.0 |

Turf quality ratings for WK 411 and other Kentucky bluegrasses for the years 1969–1971 at Rhode Island are presented in Table 6, below:

Table 6.

NE-57
Regional Project
Location: Area I — Sec.B. South
KENTUCKY BLUEGRASS VARIETY EVALUATION
University of Rhode Island
Mowing Height ¾" Low

| NO. | | TURF QUALITY 9= Ideal Turf 1= Bare Ground 1969 | 1970 | 1971 | AVERAGE |
|---|---|---|---|---|---|
| 52 | Baron | 7.8 | 7.2 | 7.1 | 7.37 abc |
| 16 | Merion | 7.7 | 7.1 | 7.1 | 7.30 a–e |
| 20 | WK 411 | 7.4 | 7.0 | 7.2 | 7.23 a–e |
| 7 | Nugget | 7.2 | 6.6 | 7.6 | 7.13 a–f |
| 26 | Belturf | 7.9 | 6.5 | 6.5 | 6.97 a–g |
| 10 | Pennstar | 7.7 | 6.5 | 6.5 | 6.90 a–g |
| 15 | Fylking | 7.8 | 6.3 | 6.5 | 6.87 a–g |
| 24 | Primo | 7.3 | 5.6 | 5.6 | 6.17 e–i |
| 3 | Windsor | 5.9 | 5.8 | 6.4 | 6.03 f–i |
| 12 | Park | 5.9 | 3.3 | 4.7 | 4.63 k–l |
| 17 | Delta | 5.7 | 3.2 | 4.6 | 4.50 l |

Values followed by the same letter are not significantly different at the 5% leve using Duncan's multiple range test.

Color ratings for WK 411 and other Kentucky bluegrasses for the years 1969–1973 at the University of Maryland are shown in Table 7, below:

Table 7.

1973 Kentucky Bluegrass Data
University of Maryland
Hopkins Research Farm
1.5" Mowing Height
Color Ratings (0–9)
9= Dark Green 0= Bleach Tan

| Variety | 1969 | 1970 | 1971 | 1972 | 1973 | Color Average |
|---|---|---|---|---|---|---|
| Windsor | 6.26 | 4.58 | 5.80 | 6.21 | 5.99 | 5.76 |
| Nugget | 6.92 | 4.20 | 6.09 | 5.92 | 6.83 | 5.89 |
| Pennstar | 7.14 | 4.54 | 5.92 | 6.59 | 6.77 | 6.19 |

Table 7.-continued

1973 Kentucky Bluegrass Data
University of Maryland
Hopkins Research Farm
1.5" Mowing Height
Color Ratings (0–9)
9= Dark Green 0= Bleach Tan

| Variety | 1969 | 1970 | 1971 | 1972 | 1973 | Color Average |
|---|---|---|---|---|---|---|
| Park | 6.26 | 4.58 | 5.05 | 5.83 | 5.72 | 5.48 |
| Fylking | 7.14 | 4.95 | 6.40 | 6.63 | 6.88 | 6.40 |
| Merion | 6.54 | 4.45 | 6.44 | 6.58 | 6.83 | 6.17 |
| Delta | 5.88 | 4.46 | 5.09 | 5.75 | 6.85 | 5.60 |
| WK-411 | 7.06 | 4.87 | 6.74 | 6.39 | 7.16 | 6.44 |
| Primo | 6.34 | 4.25 | 5.65 | 6.88 | 6.44 | 5.91 |
| Belturf | 6.74 | 4.54 | 6.09 | 6.29 | 6.16 | 5.96 |

Density ratings for WK 411 and other Kentucky bluegrasses for the years 1969–1973 are shown in Table 8, below:

Table 8.

1973 Kentucky Bluegrass Data
University of Maryland
1968 Hopkins Farm
1.5% Mowing Height
Turf Density (0–9)
9= Maximum Density 0= Bare Ground

| Variety | 1969 | 1970 | 1971 | 1972/1973 | | Density Average |
|---|---|---|---|---|---|---|
| Windsor | 7.18 | 7.58 | 6.35 | 6.25 | 6.26 | 6.72 |
| Nugget | 6.70 | 6.45 | 4.59 | 5.83 | 5.86 | 5.88 |
| Pennstar | 6.95 | 7.37 | 6.28 | 6.37 | 6.39 | 6.67 |
| Park | 7.24 | 7.04 | 6.14 | 5.08 | 5.39 | 6.17 |
| Fylking | 7.32 | 7.58 | 6.46 | 6.38 | 6.26 | 6.80 |
| Merion | 7.24 | 7.58 | 6.77 | 7.13 | 7.13 | 7.11 |
| Delta | 6.18 | 5.66 | 4.16 | 5.17 | 5.19 | 5.27 |
| WK-411 | 6.95 | 7.50 | 7.00 | 7.21 | 7.33 | 7.19 |
| Primo | 6.57 | 7.33 | 6.82 | 6.46 | 6.06 | 6.64 |
| Belturf | 7.14 | 7.66 | 6.40 | 5.71 | 5.73 | 6.53 |

As can be seen in Tables 5 and 6, WK 411 has shown consistently high turf performance. Table 7 shows that WK 411 has a very attractive dark green color, and the variety stays green from early spring (Table 5) to late fall. Table 8 indicates that WK 411 forms a very dense and good turf.

Disease Resistance

Disease resistance ratings for WK 411 and other Kentucky bluegrasses at New Brunswick, N.J. in 1972 are demonstrated in Table 9, below:

Table 9.

Regional Bluegrass Variety Test Established September 1968, at Rutgers University, New Brunswick, New Jersey.

| | Leaf Spot Percent Disease | | Stripe Smut Infected Tillers/ft.$^2$ |
|---|---|---|---|
| Variety | Apr. 10 1972 | June 5 1972 | May 10 1972 |
| Majestic | 7 | 7 | 30 |
| WK-411 | 23 | 12 | 2 |
| Fylking | 8 | 7 | 20 |
| Belturf | 27 | 33 | 26 |
| Pennstar | 10 | 8 | 14 |
| Nugget | 3 | 2 | 4 |
| Windsor | 33 | 72 | 273 |
| Merion | 68 | 33 | 433 |
| Primo | 88 | 83 | 213 |
| Park | 65 | 95 | 11 |
| Delta | 85 | 89 | 69 |
| S. Dak. Cert. | 92 | 95 | 4 |

The figures indicate that WK 411 has a very good resistance to leaf spot caused by the fungus *Helminthosporium vagans* and to stripe smut caused by the fungus *Ustilago striiformis.*

Reproduction and Propagation

Asexual reproduction of the new variety by disseminules (modified caryopses produced by agamospermy) has consistently produced progeny indistinguishable from the mother plant.

What is claimed is:

1. A new and distinct variety of Kentucky bluegrass plant, substantially as described and illustrated, characterized particularly by very good turf performance, very attractive dark green color, good rhizome and tiller development, very large seed and good resistance to leaf spot and stripe smut.

* * * * *

UNITED STATES PATENT AND TRADEMARK OFFICE

CERTIFICATE OF CORRECTION

PATENT NO. : Plant Patent No. 4165

DATED : December 13, 1977

INVENTOR(S) : Bjarne Johan Langvad

It is certified that error appears in the above-identified patent and that said Letters Patent are hereby corrected as shown below:

Column 3, between lines 45 and 46, insert Table 4 heading as follows:

-- Morphological Comparisons and Observations in WK 411 and Other Kentucky Bluegrasses (South Sweden) --.

Column 4, between lines 1 and 2, insert Table 5 heading as follows:

-- Regional Bluegrass Variety Test Established September 1968 at Rutgers University, New Brunswick, New Jersey --.

Column 4, line 30, in Table 6 column headings, insert -- NO. -- as first column heading; in second column heading, delete "NO." and replace with -- SELECTION --.

UNITED STATES PATENT AND TRADEMARK OFFICE

CERTIFICATE OF CORRECTION

PATENT NO. : Plant Patent No. 4165

DATED : December 13, 1977

INVENTOR(S) : Bjarne Johan Langvad

It is certified that error appears in the above-identified patent and that said Letters Patent are hereby corrected as shown below:

Column 4, line 39, delete "leve" and replace with -- level --.

Column 5, line 32, in Column 5 of Table 8, delete "7.13" and replace with -- 6.87 --.

Column 6, line 17, in Column 4 of Table 9, delete "4" and replace with -- 6 --.

Signed and Sealed this

*Sixth* Day of *June 1978*

[SEAL]

*Attest:*

RUTH C. MASON
*Attesting Officer*

DONALD W. BANNER
*Commissioner of Patents and Trademarks*